United States Patent
Gaw et al.

(10) Patent No.: US 9,395,295 B2
(45) Date of Patent: Jul. 19, 2016

(54) DETECTION OF CHEMICAL CHANGES OF SYSTEM FLUID VIA NEAR INFRARED (NIR) SPECTROSCOPY

(71) Applicant: The Boeing Company, Chicago, IL (US)

(72) Inventors: Kevin O. Gaw, Tukwila, WA (US); Robert E. Fisher, Everett, WA (US); Paul G. Vahey, Seattle, WA (US)

(73) Assignee: THE BOEING COMPANY, Chicago, IL (US)

( * ) Notice: Subject to any disclaimer, the term of this patent is extended or adjusted under 35 U.S.C. 154(b) by 0 days.

(21) Appl. No.: 14/485,331

(22) Filed: Sep. 12, 2014

(65) Prior Publication Data

US 2016/0076998 A1    Mar. 17, 2016

(51) Int. Cl.
| | |
|---|---|
| *G01N 21/89* | (2006.01) |
| *G01N 21/3577* | (2014.01) |
| *G01N 21/359* | (2014.01) |
| *G01N 21/31* | (2006.01) |
| *G01N 33/18* | (2006.01) |
| *G01N 21/35* | (2014.01) |

(52) U.S. Cl.
CPC .......... *G01N 21/3577* (2013.01); *G01N 21/314* (2013.01); *G01N 21/359* (2013.01); *G01N 33/18* (2013.01); *G01N 2021/3166* (2013.01); *G01N 2021/3181* (2013.01); *G01N 2021/3595* (2013.01)

(58) Field of Classification Search
CPC .................................................. G01N 21/359
See application file for complete search history.

(56) References Cited

U.S. PATENT DOCUMENTS

| | | | |
|---|---|---|---|
| 2002/0118364 A1* | 8/2002 | Amonette et al. | 356/436 |
| 2006/0266108 A1 | 11/2006 | DiFoggio | |
| 2007/0222573 A1* | 9/2007 | Navarro et al. | 340/457.4 |
| 2011/0026031 A1 | 2/2011 | Kristiansen et al. | |
| 2012/0170025 A1* | 7/2012 | Cros et al. | 356/51 |
| 2015/0021482 A1* | 1/2015 | Muller et al. | 250/341.1 |

FOREIGN PATENT DOCUMENTS

WO    2013/113666 A1    8/2013

OTHER PUBLICATIONS

Paul, et al., Chemical Contamination Sensor for Phosphate Ester Hydraulic Fluids, International Journal of Aerospace Engineering, vol. 2010, Article ID 156281.
Thomas, Teaching Mineralogy, On the Cutting Edge, Professional Development for Geoscience Faculty, Oct. 2010.
Jordan Valley AR, Inc., Quantitative Analysis of Low Levels of Chlorine and Iron in Hydraulic Oil Samples, Industry Matter, Mar. 1, 2006.
Li, FTIR and NIR Spectroscopy and Their Applications, Nutrition for Optimal Wellness, copyright 2014.

* cited by examiner

*Primary Examiner* — David Porta
*Assistant Examiner* — Hugh H Maupin
(74) *Attorney, Agent, or Firm* — MH2 Technology Law Group LLP

(57) ABSTRACT

An apparatus and method for determining quantity of water and dissolved gases in a fluid system during operation. The method and apparatus uses a sensor on the fluid system to determine the properties during operation by applying NIR (near infrared) Spectroscopy. The detection of water (including discrimination of form of water) is determined using NIR spectroscopy. In one implementation this is done by guiding a laser LED tuned to 5000-5500/cm wavenumbers and beaming the laser through a transparent window into a reservoir of fluid.

18 Claims, 4 Drawing Sheets

DETECTION OF CHEMICAL CHANGES OF SYSTEM FLUID VIA NEAR INFRARED (NIR) SPECTROSCOPY

BACKGROUND

1. Field

This disclosure relates generally to monitoring changes in a fluid system and, more particularly, to monitoring changes in water content in a hydraulic fluid system.

2. Background

The chemistry of phosphate ester based hydraulic fluid is complex and complicated by the additives that prevent corrosion and provide desirable viscosity and lubricity characteristics. The fluid deteriorates into a fluid that contains phosphoric acid with use and exposure to elevated temperatures above 160° F., which is addressed by acid acceptors added to the fluid. Fluid conductivity (to mitigate streaming charges) is enhanced by the presence of water in the fluid. Nitrogen and oxygen are present in the fluid by exposure of the fluid to the atmosphere. The changes of the fluid due to exposure due to heat, pressure, water and streaming currents can result in chemical changes to the fluid.

Maintaining the correct relationship of fluid additives with exposure of the fluids to water and oxygen prevents adverse reaction of the fluid to these conditions. Monitoring water content to control conductivity to control formation of undesirable reaction products cannot easily be done except by removing a sample from the system for analysis. The chemical changes in the fluid can be affected by exposure of the extracted sample to ambient air, which contains water as a vapor. Extracting a sample of fluid from a hydraulic system to examine it for these elements is difficult because after the sample is being extracted, its chemistry can change due to exposure to ambient conditions. An in-situ method of determining the water and oxygen content of the hydraulic fluid without opening the system to the atmosphere would be desirable.

Various types of complex spectroscopy methods have been previously used to analyze the composition of hydraulic fluid to detect changes in hydraulic fluid chemistry. Detection of out of tolerance chemical conditions using spectrographic methods including Fourier Transform Infrared (FTIR) Spectroscopy are fraught with complexity and are cumbersome for detecting hydraulic fluid water content in an operating hydraulic system.

SUMMARY

The technology as disclosed and claimed herein is an apparatus and method for determining quantity of water in a hydraulic system during operation. The method and apparatus uses a sensor on the hydraulic system (or other fluid system conducive for analysis using NIR spectroscopy) to determine fluid chemical properties during operation with the use of near infrared (NIR) Spectroscopy. The detection of water (including discrimination of form of water) is determined using NIR spectroscopy. In one implementation this is done by guiding a laser light emitting diode (LED) tuned to 5000-5500/cm (wavenumbers) [or more specifically about approximately 5155/cm wavenumbers (or a wavelength of about approximately 1940 nm)] and beaming the laser through a transparent window into a reservoir of fluid. For detection of water, other wavelengths can also be used, such as, 970 nm (10,309/cm), 1180 nm (8475/cm), and 1420 nm (7000/cm). These wavelengths are within the absorbance bands for water. The near infrared portion of the spectrum that can be utilized for this technology can be in the range of about approximately 800-2500 nm (12,500/cm to 4000/cm).

In one implementation a "baseline" spectrum (potentially using an LED), where water does not absorb, can be used as a reference. This could use a wavelength specific to hydraulic fluid (for a water content ratio), or an inactive part of the spectrum (for absolute water content). With this implementation at least two wavelengths of the electromagnetic spectrum are used. One wavelength of light is specific to water and the other wavelength of light is used to establish a ratio with the wavelength specific to water. This technology is the application of a sensor for the in-situ detection of the chemical components of a fluid in a closed fluid containing system for the purpose of system health monitoring and control of fluid quality. No in-situ measurement of water within a functioning aircraft hydraulic system is available commercially.

The proposed technology as disclosed and claimed herein will enable real-time monitoring of a fluid system's (such as a hydraulic fluid system's) water content. This technology can be a closed system of measurement that does not require sample extraction from the hydraulic system. A fluid maintenance regimen can subsequently be automated through real-time spectrographic analysis of the fluid. This analysis can be performed in real-time by a computer. This technology is the application of a sensor for the in-situ detection of chemical change or components present in the fluids [water content] in a closed fluid system for the purpose monitoring and control of fluid quality thereby enabling real-time system health monitoring.

The detection of water (including discrimination of the phase and concentration of water) can be determined using NIR spectroscopy. This can be done by guiding a laser LED of appropriate wavelength through a diamond window (or window of other compatible material such as sapphire) into a reservoir of fluid (any fluid or gas). Currently, there is not a practical means of in-situ monitoring the condition of hydraulic fluid in an airplane system, particularly as it relates to the detection of water content.

The typical method of assessing fluid condition is to: shut the hydraulic system down, depressurize the system, extract a sample of the fluid into a container and remove the sample from the aircraft for evaluation. This sample is then sent to a lab and analyzed for chemical make-up and water content. The sample however, can be affected by the extraction and handling of the sample. Oxygen content is currently not analyzed in removed samples as the process alters the concentration from what it might have been in-situ. This is due to the exposure of the sample to ambient atmospheric conditions, wherein gasses and water can be absorbed. Use of Fourier Transform Infrared (FTIR) spectroscopy and other complex spectroscopy methodologies have been previously used, but have not proven to be economical or practical nor do the methodologies directly or simply address the common sampling problem of added water content in the hydraulic fluid.

Similarly, with other fluid systems (such as fuel systems), the typical method of assessing fluid condition is also to: shut down the fluid system, in this illustration the fuel system, and extract a sample of the fluid into a container for removal and evaluation. Again, the sample can be affected by the extraction and handling. As with the hydraulic system, this is due to the exposure of the sample to ambient atmospheric conditions, wherein gasses and water can be absorbed. The NIR technology as disclosed herein can be used to detect water in most fluid systems. Each calibration and measurement would be matrix specific, but the NIR signature of water can be detected at wavelengths: 750 nm, 970 nm, 1430 nm, 1720 nm, and 1940 nm.

One implementation of the technology is a hydraulic fluid monitoring apparatus, which includes a hydraulic fluid line having a closed side wall where said closed side wall has a window portion and said window portion is composed of a material allowing light, and particularly a near infrared emitted/reflected light to pass there through. The window can be constructed of a transparent material and can have optical characteristics such that such that near infrared emitted light can pass through without significant loss. The technology can further comprise a light source configured to direct near infrared emitted light through said window for energizing and illuminating the fluid flowing through a hydraulic fluid line. The apparatus can include and integral or separate spectrometric sensor having an optical filter adapted to pass reflected near infrared light that is reflected outwardly through said window after contacting the fluid. The near infrared reflected light is passed to a near infrared detector adapted to determine a radiation absorption value about a wavelength conducive for determining percent water content. The technology as disclosed and claimed can utilize a narrow band or specific wavelength for the purpose of analyzing radiation absorption within that narrow or specific band, which provide the information needed to determine percent weight of water in the hydraulic fluid.

One implementation of the hydraulic fluid monitoring apparatus will analyze radiation absorption at a wavelength conducive for determining percent water content that is in the range of about 5000/cm to about 5500/cm. The apparatus can analyze the radiation absorption at a specific wavelength that is at about approximately 5200/cm. In one implementation of the apparatus the light source can be a near infrared light emitting diode.

For the purpose of analyzing the radiation absorption measurements reflective of the percent water content in the hydraulic fluid in-situ, the spectrometric apparatus of the hydraulic fluid monitoring apparatus can be coupled to a computing system having a processor and a memory, where said memory can have electronically stored thereon processor executable program instructions where when said processor executable program instructions are executed and adapted to cause said computing system to receive the radiation absorption value, determine a weight percent of water and generate a maintenance message if the weight percent of water is outside of a specified range or deviates from a predetermined value.

In order to correct the hydraulic fluid composition, if by way of illustration the weight percent of water is outside of a specified range or deviates from a predetermined value, one implementation of the hydraulic fluid monitoring apparatus further includes an injector of fluid in fluid communication with the hydraulic fluid line and configured to selectively inject one or more of gas, solution and/or water into the hydraulic fluid line responsive to the maintenance message. In one implementation the memory of the computing system includes and execute executable program instructions where when executed, cause the computing system to determine an additive amount of one or more components (gas, solution and/or water) that should be injected into the hydraulic fluid line. Source(s) (e.g. fluid, solution and gas sources) for one or more components can be communicably linked to the injector.

In one implementation the hydraulic fluid monitoring apparatus can have the closed hydraulic fluid line having the closed side wall where said closed side wall has the window portion and the window portion is composed of a material allowing light to pass there through. Opposite the window portion, the apparatus can further include an exit portal portion of the closed sidewall composed of the same material as the window portion and said exit portal portion can be on the opposing side of the closed sidewall with respect to the window portion and in line with said window portion. The exit portal portion can be adapted to pass through near infrared light transmitted through the exit portal portion to a near infrared detector adapted to determine a radiation absorption value about a wavelength conducive for determining percent water content. With this implementation the spectrometric sensor having said optical filter adapted to pass near infrared light received outwardly through said exit portal portion to the near infrared detector and adapted to determine a radiation absorption value about the wavelength conducive for determining percent water content, can be positioned to receive light passing through the exit portal.

In one implementation of the technology a method for determining the composition of hydraulic fluid can include directing near infrared emitted light from a light source through a window portion of a closed sidewall of a closed hydraulic fluid line where said window portion is composed of a material allowing light to pass there through. The method can further include sensing and filtering near infrared reflected light with a spectrometric sensor having an optical filter adapted to pass the reflected near infrared light reflected outwardly through said window and further include detecting the reflected near infrared light with a near infrared detector and determining a radiation absorption value about a wavelength conducive for determining percent water content. Again, this technology is the application of a sensor for the in-situ detection of components of fluid in a closed fluid containing system for the purpose of system health monitoring and control of fluid quality.

The features, functions, and advantages that have been discussed can be achieved independently in various embodiments or may be combined in yet other embodiments further details of which can be seen with reference to the following description and drawings.

These and other advantageous features of the present invention will be in part apparent and in part pointed out herein below.

BRIEF DESCRIPTION OF THE DRAWINGS

For a better understanding of the present invention, reference may be made to the accompanying drawings in which.

Figure 1:
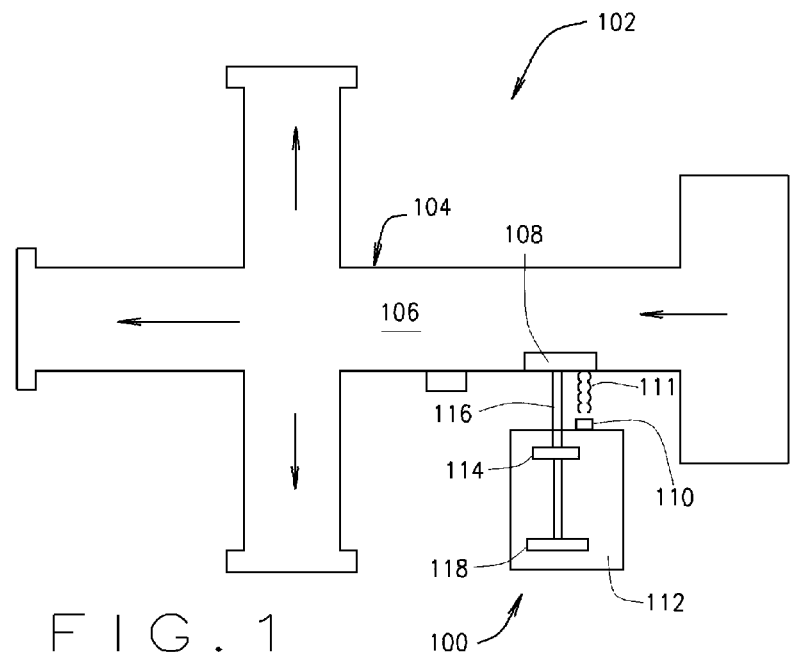
FIG. 1 is an illustration of a fluid monitoring apparatus for monitoring through a single viewing window, in reflectance mode.

While the invention is susceptible to various modifications and alternative forms, specific embodiments thereof are shown by way of example in the drawings and will herein be described in detail. It should be understood, however, that the drawings and detailed description presented herein are not intended to limit the invention to the particular embodiment disclosed, but on the contrary, the intention is to cover all modifications, equivalents, and alternatives falling within the spirit and scope of the present invention as defined by the appended claims.

DESCRIPTION

According to the implementation(s) of the present technology as disclosed and claimed herein, various views are illustrated in FIGS. 1-6 and like reference numerals are being used consistently throughout to refer to like and corresponding parts of the invention for all of the various views and figures of the drawing. Also, please note that the first digit(s) of the reference number for a given item or part of the technology as described herein should correspond to the Fig. number in which the item or part is first identified.

One implementation of the present disclosure comprising a spectrometric sensor system for determining a radiation absorption value about a wavelength conducive for determining percent water content teaches a novel apparatus and method for detecting excess water in a hydraulic fluid line.

The details of the disclosure and various implementations can be better understood by referring to the figures of the drawing. Referring to FIG. 1, a hydraulic fluid monitoring apparatus 100 is shown communicably attached to a hydraulic fluid system 102. A hydraulic fluid line 104 is illustrated having a closed side wall 106 to affect a closed hydraulic system. The closed side wall 106 is illustrated having on one side a window portion 108 and the window portion 108 can be composed of a material allowing emitted light to pass there through. A light source 110 positioned adjacent the window portion 108 can be configured to direct near infrared emitted light 111 through the window portion 108.

A spectrometric sensor 112 having an optical filter 114 adapted to pass reflected near infrared light 116 reflected outwardly through said window portion 108 to a near infrared detector 118 adapted to determine a radiation absorption value about a wavelength conducive for determining percent water content. With this implementation, scattered light will also pass through the window and will be detected. The current implementation of the technology has determined that an optimal wavelength conducive for determining percent water content is in the range of about 5000/cm to about 5500/cm (The Near-IR region includes several overtones of water, which means it can be sensed at multiple wavelengths including 970 nm, 1180 nm, 1410 nm and 1940 nm). More specifically the wavelength can be at about 5200/cm. The light source 110 can be a near infrared light emitting diode.

Figure 2:
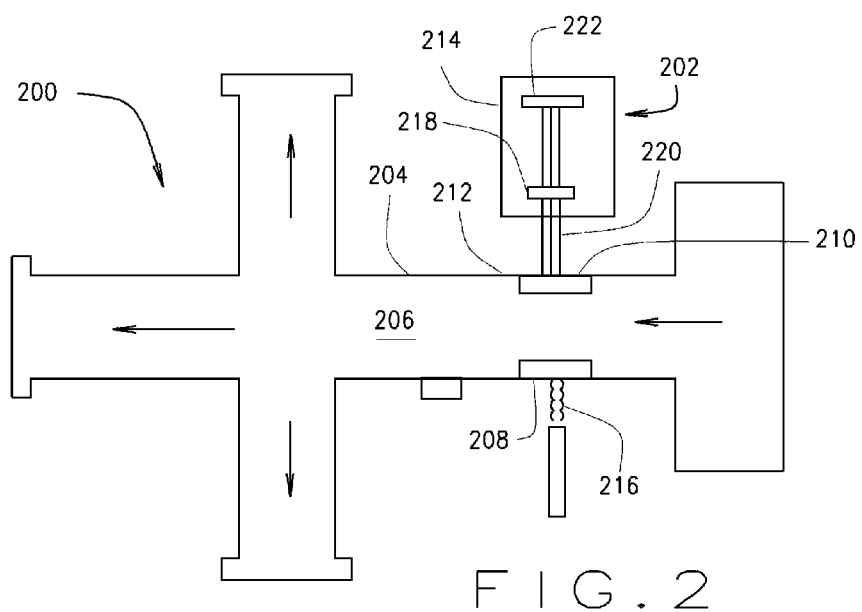
FIG. 2 is an illustration of a fluid monitoring system for monitoring through two viewing windows, in transmission mode.

Referring to FIG. 2, another implementation of a hydraulic fluid monitoring apparatus 202 as is shown where the closed hydraulic fluid line 204 of a hydraulic fluid system 200 is shown having a closed side wall 206 forming the closed system. The closed side wall 206 can have a window portion 208 and the window portion 208 can be composed of a material allowing light to pass there through. However, with this implementation there can be an exit portal portion 210 of the closed sidewall 206 composed of the same material as the window portion 208 and said exit portal portion 210 is on the opposing side 212 of the closed sidewall 206 with respect to the window portion and adapted to pass through near infrared light transmitted through said exit portal portion 210.

Again a spectrometric sensor 214 can be adapted to determine a radiation absorption value about a wavelength conducive for determining percent water content. A spectrometric sensor 214 can be utilized having said optical filter 218 adapted to pass near infrared pass-through light 220 received outwardly through said exit portal portion 210 to a near infrared detector 222 adapted to determine a radiation absorption value about a wavelength conducive for determining percent water content. The emitted light 216 will interact with the sample and will be at least partially absorbed by the sample through which the light is transmitted. In one implementation a "baseline" LED in another part of the spectrum, where water does not absorb, can be used as a reference.

Figure 3:
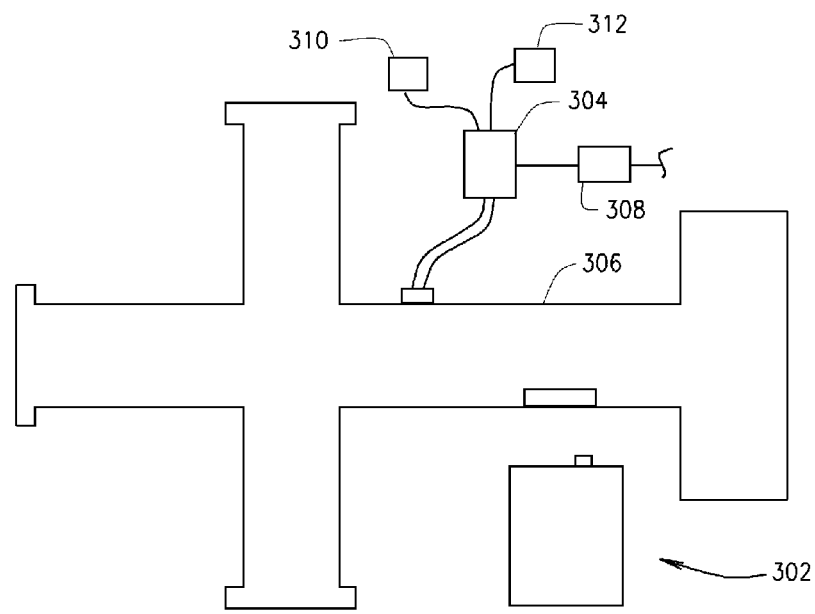
FIG. 3, is an illustration of an injector coupled to a source.

Referring to FIG. 3, the hydraulic fluid monitoring apparatus 302 is illustrated including an injector 304 in fluid communication with the hydraulic fluid line 306 and configured to selectively inject one or more of air and water into the hydraulic fluid line 306 responsive to a maintenance message. The injector can be controlled by a controller device 308 adapted to receive electronic indicators or signals representative of maintenance messages providing information to the controller. The controller device 308 can control the injector 304 to selectively inject one or more air and water in the hydraulic fluid line if it has been determined that the hydraulic fluid composition is out of tolerance and air and/or water should be injected to bring the composition back within tolerance. One or more of an air source 310 and a water source 312 communicably linked to the injector 304.

Figure 4:
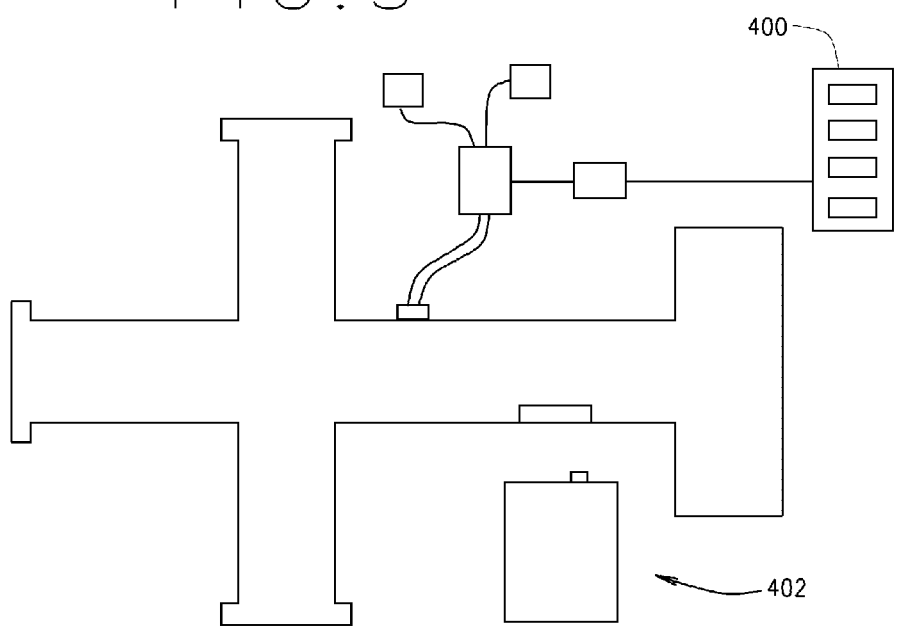
FIG. 4, is an illustration of a computing device couples to the system.

Referring to FIG. 4, an illustration of a computing device 400 coupled to the system 402 is provided. A computing system 402 is illustrated having a processor and a memory. The memory having electronically stored thereon processor executable program instructions where when said processor executable program instructions are executed, they will cause the computing system to receive the radiation absorption value, determine a percentage of water and to generate a maintenance message if the percentage of water is outside of a predetermined range or value. The processor executable program instructions can also be executed to cause the computing system to determine an additive amount of one or more of air and water that should be injected into the hydraulic fluid line. The computing system can generate a maintenance message having imbedded instructions to be sent to a controller of an injector to instruct the injector the amount of water and/or air should be injected into the system.

Figure 5:
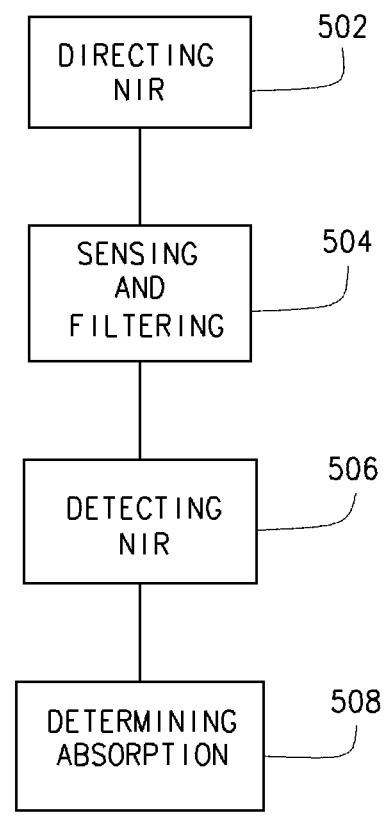
FIG. 5, is an illustration of the process to determine percent weight water.

Referring to FIG. 5, an illustration of the process to determine percent weight water is shown. One implementation of the process can include determining the composition of hydraulic fluid comprising by directing near infrared emitted light 502 from a light source through a window portion of a closed sidewall of a closed hydraulic fluid line where said window portion is composed of a material allowing light to pass there through. The process can further include sensing and filtering with a spectrometric sensor 504 having an optical filter adapted to pass reflected near infrared light reflected outwardly through said window. The process can also include detecting the reflected near infrared light 506 with a near infrared detector and determining a radiation absorption value 508 about a wavelength (or wavelengths) conducive for determining percent water content. The wavelength conducive for determining percent water content can be in the range of about 5000/cm to about 5500/cm. More specifically the wavelength can be at about 5200/cm. The process can include using a light source that is a near infrared light emitting diode.

The process can also include executing program instructions electronically stored in a memory of a computing system with a processor of the computing system where executing said program instructions includes, receiving at the computer system the radiation absorption value, determining a weight percent of water, and generating a maintenance message if the weight percent of water is greater than a predetermined value. The computing system can be used to perform the process of controlling the selectively injecting one or more of air and water into the hydraulic fluid line responsive to the maintenance message with an injector in fluid communication with said hydraulic line, where executing said program instructions include, determining an additive amount of one or more of air and water that should be injected into the hydraulic fluid line.

The process can also include providing one or more of an air source and a water source to the injector. In yet another implementation using a window portion and an exit portal portion can perform the process of passing the near infrared light through an exit portal portion of the closed sidewall composed of the same material as the window portion and the exit portal portion is on the opposing side of the closed sidewall with respect to the window portion. The process can also include sensing and filtering with the spectrometric sensor having the optical filter is adapted to pass transmitted near infrared light transmitted outwardly through said exit portal portion to a near infrared detector adapted to determine the radiation absorption value about the wavelength conducive for determining percent water content.

In the case of using both a window portion and an exit portal portion process for determining the composition of hydraulic fluid can include directing near infrared emitted light from a light source through a window portion of a closed sidewall of a closed hydraulic fluid line where the window portion is composed of a material allowing light to pass there through. The process can include sensing and filtering with a spectrometric sensor having an optical filter adapted to pass reflected near infrared light reflected outwardly through said window. Yet another process step can be detecting the reflected near infrared light with a near infrared detector and determining a radiation absorption value about a wavelength conducive for determining percent water content.

The process can also execute program instructions electronically stored in a memory of a computing system with a processor of said computing system where executing said program instructions includes, receiving at the computer system the radiation absorption value, determining a weight percent of water, and generating a maintenance message if the weight percent of water is greater than a predetermined value. The process can further include selectively injecting one or more of air and water into the hydraulic fluid line responsive to the maintenance message with an injector in fluid communication with said hydraulic line. Executing said program instructions can include, determining an additive amount of one or more of air and water that should be injected into the hydraulic fluid line, and providing one or more of an air source and a water source to the injector.

In yet another implementation of the hydraulic fluid monitoring apparatus comprising a spectrometric system as described above, can include a light source configured to direct near infrared emitted light through a window of a hydraulic line. A spectrometric sensor can have an optical filter adapted to pass reflected near infrared light reflected outwardly through said window to a near infrared detector adapted to determine a radiation absorption value about a wavelength conducive for determining percent water content. The wavelength conducive for determining percent water content can be in the range of about 5000/cm to about 5500/cm.

Figure 6:
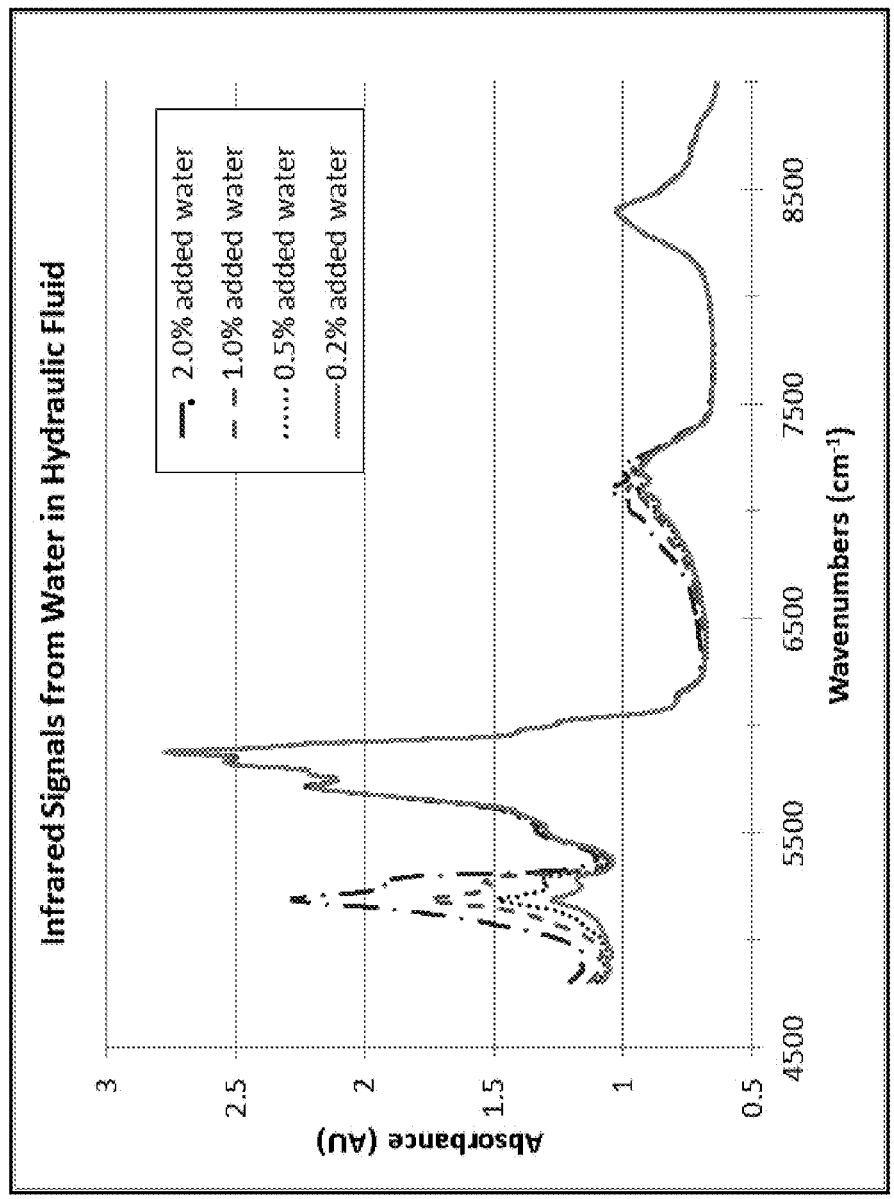
FIG. 6 is an illustration of a graphical representation of absorption of near infrared emitted light.

FIG. 6 is an illustration of a graphical representation of absorption of near infrared emitted light. The graphical representation illustrates the narrow bands over which absorption can be readily determined as it relates to humidity. You can see the significant difference at 5000/cm (1940 nm) and 7000/cm (1420 nm).

The various implementations and examples shown above illustrate a method and system for determining a radiation absorption value about a wavelength conducive for determining percent water content teaches a novel apparatus and method for detecting excess water in a hydraulic fluid line. A user of the present method and system may choose any of the above implementations, or an equivalent thereof, depending upon the desired application. In this regard, it is recognized that various forms of the subject spectrometric method and system could be utilized without departing from the scope the specification and claims.

As is evident from the foregoing description, certain aspects of the present implementation are not limited by the particular details of the examples illustrated herein, and it is therefore contemplated that other modifications and applications, or equivalents thereof, will occur to those skilled in the art. It is accordingly intended that the claims shall cover all such modifications and applications that do not depart from the spirit and scope of the present implementation. Accordingly, the specification and drawings are to be regarded in an illustrative rather than a restrictive sense.

Certain systems, apparatus, applications or processes are described herein as including a number of modules. A module may be a unit of distinct functionality that may be presented in software, hardware, or combinations thereof. When the functionality of a module is performed in any part through software, the module includes a computer-readable medium. The modules may be regarded as being communicatively coupled. The inventive subject matter may be represented in a variety of different implementations of which there are many possible permutations.

The methods described herein do not have to be executed in the order described, or in any particular order. Moreover, various activities described with respect to the methods identified herein can be executed in serial or parallel fashion. In the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter may lie in less than all features of a single disclosed embodiment. Thus, the following claims are hereby incorporated into the Detailed Description, with each claim standing on its own as a separate embodiment.

In an example implementation, the machine operates as a standalone device or may be connected (e.g., networked) to other machines. In a networked deployment, the machine may operate in the capacity of a server or a client machine in server-client network environment, or as a peer machine in a peer-to-peer (or distributed) network environment. The machine may be a server computer, a client computer, a personal computer (PC), a tablet PC, a set-top box (STB), a Personal Digital Assistant (PDA), a cellular telephone, a web appliance, a network router, switch or bridge, or any machine capable of executing a set of instructions (sequential or otherwise) that specify actions to be taken by that machine or computing device. Further, while only a single machine is illustrated, the term "machine" shall also be taken to include any collection of machines that individually or jointly execute a set (or multiple sets) of instructions to perform any one or more of the methodologies discussed herein.

The example computer system 400 and client computers 406, 408, 410 include a processor (e.g., a central processing unit (CPU) a graphics processing unit (GPU) or both), a main memory and a static memory, which communicate with each other via a bus. The computer system may further include a video/graphical display unit (e.g., a liquid crystal display (LCD) or a cathode ray tube (CRT)). The computer system 400 and client computing devices 406, 408, 410 also include an alphanumeric input device (e.g., a keyboard), a cursor control device (e.g., a mouse), a drive unit, a signal generation device (e.g., a speaker) and a network interface device.

The drive unit includes a computer-readable medium on which is stored one or more sets of instructions (e.g., software or program) embodying any one or more of the methodologies or systems described herein. The instructions when executed or processed by the computing device can cause the machine, computer, or otherwise to perform a process and provide a tangible and useful result. The software may also reside, completely or at least partially, within the main memory and/or within the processor during execution thereof by the computer system, the main memory and the processor also constituting computer-readable media. The software may further be transmitted or received over a network via the network interface device.

The term "computer-readable medium" should be taken to include a single medium or multiple media (e.g., a centralized or distributed database, and/or associated caches and servers) that store the one or more sets of instructions. The term "computer-readable medium" shall also be taken to include any medium that is capable of storing or encoding a set of instructions for execution by the machine and that cause the machine to perform any one or more of the methodologies of the present implementation. The term "computer-readable medium" shall accordingly be taken to include, but not be limited to, solid-state memories, and optical media, and magnetic media.

As is evident from the foregoing description, certain aspects of the present disclosure are not limited by the particular details of the examples illustrated herein, and it is therefore contemplated that other modifications and applications, or equivalents thereof, will occur to those skilled in the art. It is accordingly intended that the claims shall cover all such modifications and applications that do not depart from the spirit and scope of the specification and claims.

Other aspects, objects and advantages of the present disclosure can be obtained from a study of the drawings, the disclosure and the appended claims.

What is claimed is:

1. A fluid monitoring apparatus comprising:
    a fluid line having a closed side wall where said closed side wall has a window portion and said window portion is composed of a material that allows a near infrared emitted light to pass there through;
    a light source configured to direct the near infrared emitted light through said window portion;
    a spectrometric sensor having an optical filter adapted to pass reflected near infrared light reflected outwardly through said window portion to a near infrared detector adapted to determine a radiation absorption value about a wavelength conducive for determining percent water content;
    and
    an injector in fluid communication with the fluid line and configured to selectively inject one or more of air and water into the fluid line responsive to a maintenance message indicative of the percent water content.

2. The fluid monitoring apparatus as recited in claim 1, where said wavelength conducive for determining percent water content is in a range of about 5000/cm to about 5500/cm.

3. The fluid monitoring apparatus as recited in claim 2, where said wavelength conducive for determining percent water content is at about 5200/cm.

4. The fluid monitoring apparatus as recited in claim 1, where the fluid line is a hydraulic fluid line and where the light source is a near infrared light emitting diode.

5. The fluid monitoring apparatus as recited in claim 1, further comprising:
    a computing system having a processor and a memory;
    said memory having electronically stored thereon processor executable program instructions where when said processor executable program instructions are executed are adapted to cause said computing system to receive a radiation absorption value, determine a weight percent of water and to generate the maintenance message if the weight percent of water is greater than a predetermined value.

6. The fluid monitoring apparatus as recited in claim 5, where when said processor executable program instructions are executed causing said computing system to determine an additive amount of one or more of air and water that should be injected into the fluid line.

7. The fluid monitoring apparatus as recited in claim 6, further comprising:
    one or more of an air source and a water source communicably linked to the injector.

8. The fluid monitoring apparatus as recited in claim 1, where the fluid line having the closed side wall where said closed side wall has the window portion and said window portion is composed of the material that allows a near infrared emitted light to pass there through, further comprises:
    an exit portal portion of the closed sidewall composed of a same material as the window portion that allows the near infrared emitted light to pass and said exit portal portion is on an opposing side of the closed sidewall with respect to the window portion and adapted to pass through the near infrared emitted light transmitted through said exit portal portion to a near infrared detector adapted to determine the radiation absorption value about the wavelength conducive for determining percent water content; and
    said spectrometric sensor having said optical filter adapted to pass the near infrared emitted light received outwardly through said exit portal portion to the near infrared detector adapted to determine the radiation absorption value about the wavelength conducive for determining percent water content.

9. A method for determining a composition of fluid comprising:
    directing near a infrared emitted light from a light source through a window portion of a closed sidewall of a closed fluid line where said window portion is composed of a material allowing the near infrared emitted light to pass there through;
    sensing and filtering with a spectrometric sensor having an optical filter adapted to pass a reflected near infrared light reflected outwardly through said window portion;
    detecting the reflected near infrared light with a near infrared detector and determining a radiation absorption value about a wavelength conducive for determining percent water content;
    and
    selectively injecting one or more of air and water into the fluid line responsive to a maintenance message indicative of the percent water content with an injector in fluid communication with said fluid line.

10. The method as recited in claim 9, where said wavelength conducive for determining percent water content is in a range of about 5000/cm to about 5500/cm.

11. The method as recited in claim 10, where said wavelength conducive for determining percent water content is at about 5200/cm.

12. The method as recited in claim 9, where the light source is a near infrared light emitting diode.

13. The method as recited in claim 9, further comprising:
executing program instructions electronically stored in a memory of a computing system with a processor of said computing system where executing said program instructions includes,
receiving at the computer system the radiation absorption value,
determining a percentage of water, and
generating the maintenance message if the weight percent of water is outside of a predetermined range.

14. The method as recited in claim 13, where executing said program instructions include, determining an additive amount of one or more of air and water that should be injected into the fluid line in order to restore a fluid in the fluid line to a predetermined composition.

15. The method as recited in claim 14, further comprising:
providing one or more of an air source and a solution source to the injector.

16. The method as recited in claim 9, further comprising:
passing the near infrared emitted light through an exit portal portion of the closed sidewall composed of a same material as the window portion that allows the near infrared emitted light to pass as the window portion and said exit portal portion is on the opposing side of the closed sidewall with respect to the window portion,
where sensing and filtering with the spectrometric sensor having the optical filter is adapted to pass transmitted near infrared light transmitted outwardly through said exit portal portion to a near infrared detector adapted to determine the radiation absorption value about the wavelength conducive for determining percent water content.

17. A fluid monitoring apparatus comprising:
a spectrometric system including a light source configured to direct near infrared emitted light through a window portion of a hydraulic line;
a spectrometric sensor having an optical filter adapted to pass reflected near infrared light reflected outwardly through said window to a near infrared detector adapted to determine a radiation absorption value about a wavelength conducive for determining percent water content;
a computing system having a processor and a memory;
said memory having electronically stored thereon processor executable program instructions where when said processor executable program instructions are executed are adapted to cause said computing system to receive the radiation absorption value, determine a weight percent of water and to generate a maintenance message if the weight percent of water is greater than a predetermined value;
and
an injector in fluid communication with the hydraulic line and configured to selectively inject one or more of air and water into the hydraulic line responsive to the maintenance message.

18. The fluid monitoring apparatus as recited in claim 17, where said wavelength conducive for determining percent water content is in a range of about 5000/cm to about 5500/cm.

* * * * *